United States Patent
Childress et al.

(10) Patent No.: US 10,001,445 B2
(45) Date of Patent: Jun. 19, 2018

(54) VISION SYSTEM

(71) Applicant: RING CONTAINER TECHNOLOGIES, Oakland, TN (US)

(72) Inventors: Jeff Childress, Bartlett, TN (US); Sam Kerley, Arlington, TN (US); Danny Wayne VanPelt, Hernando, MS (US)

(73) Assignee: Ring Container Technologies, LLC, Oakland, TN (US)

( * ) Notice: Subject to any disclaimer, the term of this patent is extended or adjusted under 35 U.S.C. 154(b) by 432 days.

(21) Appl. No.: 13/628,641

(22) Filed: Sep. 27, 2012

(65) Prior Publication Data
US 2013/0076891 A1 Mar. 28, 2013

Related U.S. Application Data

(60) Provisional application No. 61/539,609, filed on Sep. 27, 2011.

(51) Int. Cl.
*G01N 21/90* (2006.01)

(52) U.S. Cl.
CPC ....... *G01N 21/9081* (2013.01); *G01N 21/909* (2013.01)

(58) Field of Classification Search
CPC .............................................. G01N 2033/0081
USPC ......................................................... 348/127
See application file for complete search history.

(56) References Cited

U.S. PATENT DOCUMENTS

| | | | | |
|---|---|---|---|---|
| 4,974,261 A * | 11/1990 | Nakahara | ............... | G01N 21/88 348/128 |
| 5,095,204 A * | 3/1992 | Novini | ............... | G01N 21/9045 250/223 B |
| 5,187,573 A * | 2/1993 | Yoshida | ............... | G01N 21/8851 250/223 B |
| 5,321,767 A * | 6/1994 | Murase | ................... | G06T 7/004 348/130 |
| 5,392,928 A * | 2/1995 | Nickey | ................. | B07C 5/3404 198/460.1 |
| 5,864,395 A * | 1/1999 | Laurberg | ........... | G01N 21/9027 250/223 B |
| 5,926,268 A * | 7/1999 | Bonewitz | .............. | B07C 5/3416 356/240.1 |
| 6,295,374 B1 * | 9/2001 | Robinson | ............... | G06K 9/036 348/95 |
| 6,665,363 B1 * | 12/2003 | Mahe | ..................... | G21C 17/06 376/245 |
| 2002/0039183 A1 * | 4/2002 | Yagita | ................ | G01N 21/9081 356/240.1 |

(Continued)

OTHER PUBLICATIONS

Peng et al. ("An online defects inspection method for float glass fabrication based on machine vision," Int J adv Manuf Technol (2008) 39: 1180-1189).*

(Continued)

*Primary Examiner* — William C Vaughn, Jr.
*Assistant Examiner* — Stuart Bennett
(74) *Attorney, Agent, or Firm* — Sorell Lenna & Schmidt, LLP (57) ABSTRACT

Provided is a vision system for detecting a defect, including a conveyer belt configured to move at least one bottle through the vision system; a light emitting diode (LED) backlight configured to silhouette any dark contamination on a surface or inside the at least one bottle; a robot with a bottle gripper tooling, the robot configured to pick up the at least one bottle and rotate the at least one bottle; at least one camera configured to take pictures of the at least one bottle while the at least one bottle is being rotated; and a flipper arm configured to stop or allow the at least one bottle to move to a position where the robot picks up the at least one bottle.

9 Claims, 8 Drawing Sheets

(56) References Cited

U.S. PATENT DOCUMENTS

2002/0157919 A1* 10/2002 Sherwin .................. B65G 1/08
  193/37
2008/0309339 A1* 12/2008 Chisholm ............ G01N 24/087
  324/315

OTHER PUBLICATIONS

Peng et al. ("An online defects inspection method for float glass fabrication based on machine vision," Int J Adv Manuf Technol (2008) 39:1190-1189).*

Peng et al. "An online defects inspection method for float glass fabrication based on machine vision," Int J Adv Manuf Technol (2008) 39:1190-1189.*

* cited by examiner

HMI REJECT ZONES SCREEN

HMI REJECT COUNTS SCREEN

VISION SYSTEM

CROSS-REFERENCE TO RELATED APPLICATION

This application claims priority under 35 USC § 119 to U.S. Provisional Application No. 61/539,609, filed Sep. 27, 2011, the contents of which are herein incorporated by reference in its entirety.

BACKGROUND

1. Technical Field

Embodiments relate to a vision system. More particularly, embodiments relate to a vision system for inspecting and identifying defects in a bottle.

2. Description of the Related Art

In a related art field, there are several different systems for inspecting and identifying bottle defects. For example, in the related art, there may be a leak inspector (i.e., a human) that manually inspects bottles traveling through an assembly line. However, as there is a need for increasing the efficiency and output of a bottle assembly line, the leak inspector may not have enough time to thoroughly investigate and identify bottle defects. Further, if the bottle is not clear, the leak inspector may only be able to see defects on the surface of the bottle. However, defects of a bottle can occur both on the surface of the bottle and inside the bottle. As bottles are moving to lightweight plastic, more small defects are being introduced inside the bottle (i.e., unmelted resin or gel) rather than carbon char, dust, etc., on the outside of the bottle. Thus, the leak inspector may not have enough time to identify bottle defects. Also, the leak inspector may not be able to see the small defects that are being introduced inside the bottle.

In another example of the related art, to identify defects, a related art system can use a surface light and a camera to take pictures of a bottle. However, if the bottle is not clear, the camera would not be able to see defects inside the bottle. Therefore, the camera would only be able to see defects on the surface of the bottle. Thus, using only a surface light and a camera is not an effective way for detecting defects on the surface and inside the bottle.

In another example of the related art, line scan cameras can be used to see cross sectional sheets of a bottle. However, line scan cameras only work well with clear plastic bottles (such as polyethylene terephthalate, or PET), which allow for defects to be detected inside and outside the bottles. However, line scan cameras are not good for non-clear bottles. Further, if the bottle has a non-uniform texture, inaccurate defects may be detected by the line scan cameras. In other words, the line scan cameras may identify the non-uniform texture as a defect.

If small defects are not detected in the bottle containers, this could cause problems for the end customer. Usually, many bottles are shipped to the end customer, and are stacked on top of one another. If a small defect inside a bottle causes a leak, all of the contents could be leaked out, and could ruin the remaining bottles. Therefore, the end customer wants to reduce the number of defects in bottles. Thus, there is a need for a system which can detect defects inside and outside of the bottle. Further, the system must be able to adapt to bottles that are non-clear and have a non-uniform texture.

SUMMARY

Exemplary embodiments provide a vision system for detecting bottle defects.

According to one aspect of the embodiments, a vision system for detecting a defect may include a conveyer belt configured to move at least one bottle through the vision system; a light emitting diode (LED) backlight configured to silhouette any dark contamination on a surface or inside the at least one bottle; a robot with a bottle gripper tooling, the robot configured to pick up the at least one bottle and rotate the at least one bottle; at least one camera configured to take pictures of the at least one bottle while the at least one bottle is being rotated; and a flipper arm configured to stop or allow the at least one bottle to move to a position where the robot picks up the at least one bottle.

The defect in the at least one bottle may be detected by determining whether grayscale values of each picture taken by the at least one camera is greater than a threshold value.

The threshold value may be determined by calculating a mean grayscale value of each picture.

If the defect in the at least one bottle is detected, the at least one bottle may be rejected.

The LED backlight may be taller and wider than the at least one bottle to allow light to penetrate all sides of the at least one bottle.

The robot with the bottle gripping tooling may pick up the at least one bottle from a top of the at least one bottle using suction cups.

The flipper arm may allow the at least one bottle to move to the position where the robot picks up the at least one bottle when the position where the robot picks up the at least one bottle is clear.

The flipper arm may stop the at least one bottle from moving to the position where the robot picks up the at least one bottle when the position where the robot picks up the at least one bottle is not clear.

At least one photo-eye may detect whether the position where the robot picks up the at least one bottle is clear or not.

A side conveyer may grip the at least one bottle in mid-air, the side conveyer gripping the at least one bottle before the at least one bottle reaches the position where the robot picks up the at least one bottle.

According to another aspect of the embodiments, a method of detecting defects in a vision system may include inputting a picture, taken by at least one camera, of at least one bottle; inputting manual regions, each manual region defined by a plurality of zones, which correspond to the picture taken by the at least one camera; performing a histogram by calculating grayscale values of each zone; setting a threshold value of each zone based on the histogram; comparing the threshold value of each zone with the calculated grayscale values; and rejecting the at least one bottle if any of the calculated grayscale values is greater than the threshold value of each zone.

The manual regions may be defined by a user.

The manual regions may exclude regions where the grayscale values are always greater than the predetermined threshold.

The manual regions may correspond to the picture by having a same shape as the picture taken by the at least one camera.

The setting the threshold value based on each zone based on the histogram may further include calculating a mean grayscale value of each zone; and setting the threshold value based on the mean grayscale value of each zone.

Stopping the defect detection may occur when the at least one bottle is rejected.

Repeating the defect detection may occur for another picture taken by at least one camera when the at least one bottle is not rejected.

The performing the histogram by calculating grayscale values of each zone may further include sweeping through each zone and calculating grayscale values at predetermined interval points of each zone.

According to another further aspect of the embodiments, a method of defecting defects in a vision system may include inputting a picture, taken by at least one camera, of at least one bottle; inputting a large manual region, the large manual region corresponding to the picture taken by the at least one camera; inputting a small manual region for sequentially sweeping through the large manual region, the small region corresponding to the large manual region; performing a histogram by calculating grayscale values of each small region; setting a threshold value of each small region based on the histogram; comparing the threshold value of each small region with the calculated grayscale values; and rejecting the at least one bottle if any of the calculated grayscale values is greater than the threshold value of each small region.

The small manual region may correspond to the large manual region by having a same shape.

The large manual region may correspond to the picture by having a same shape as the picture taken by the at least one camera.

The setting the threshold value based on each small manual region based on the histogram may further include calculating a mean grayscale value of each small manual region; and setting the threshold value based on the mean grayscale value of each small manual region.

The performing the histogram by calculating grayscale values of each small region may further include sweeping each small manual region through the large manual region and calculating grayscale values at predetermined interval points of each small manual region.

The small manual region and the large manual region may be defined by a user.

BRIEF DESCRIPTION OF THE DRAWINGS

Illustrative, non-limiting example embodiments will be more clearly understood from the following detailed description, taken in conjunction with the accompanying drawings.

DETAILED DESCRIPTION OF THE EMBODIMENTS

Various example embodiments will be described more fully hereinafter with reference to the accompanying drawings, in which some example embodiments are shown. Example embodiments may, however, be embodied in many different forms and should not be construed as limited to the example embodiments set forth herein. Rather, these example embodiments are provided so that this disclosure will be thorough and complete, and will fully convey the scope of the embodiments to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these elements should not be limited by these terms. These terms are used to distinguish one element from another. Thus, a first element discussed below could be termed a second element without departing from the teachings of the present embodiments. As used herein, the term "and/or" includes any and all combinations of one or more of the associated listed items.

It will be understood that when an element is referred to as being "connected", "attached", or "coupled" to another element, it can be directly connected, attached, coupled to the other element or intervening elements may be present. In contrast, when an element is referred to as being "directly connected", "directly attached", or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which these embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
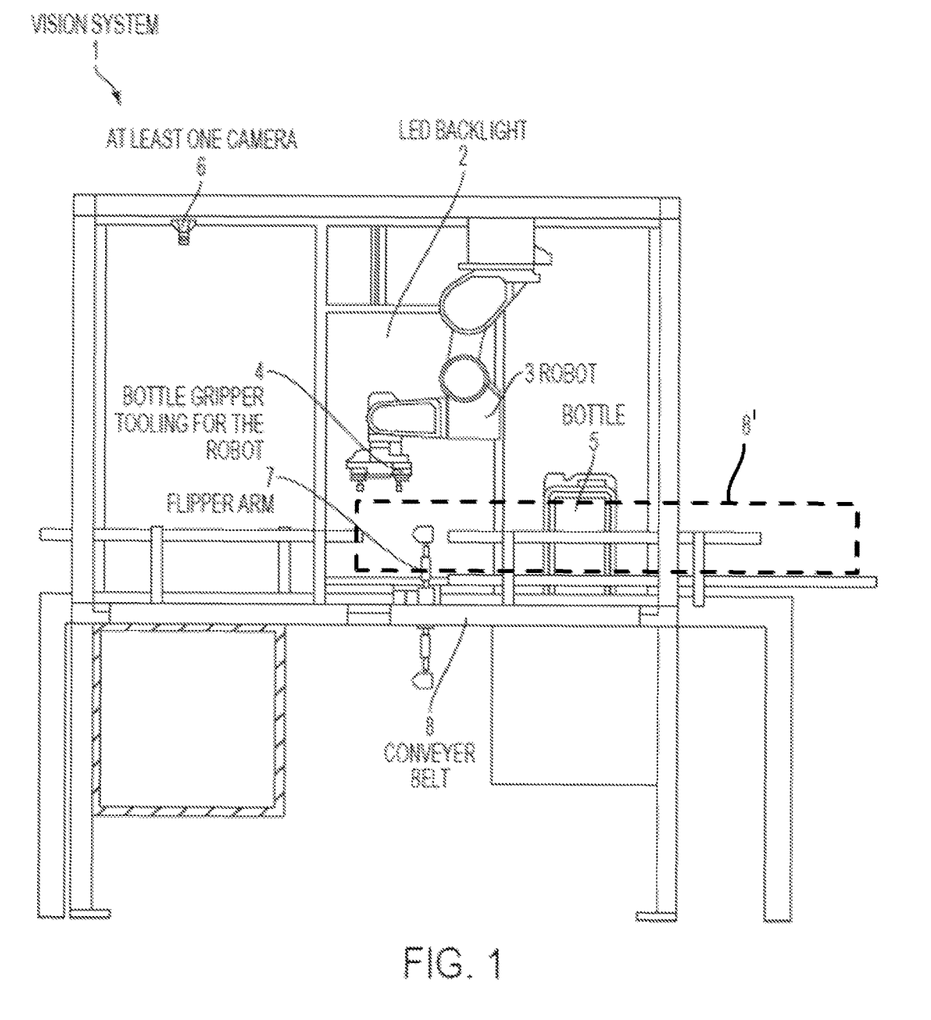
FIG. 1 is a diagram illustrating a first exemplary embodiment of a vision system.

FIG. 1 is a diagram illustrating a first exemplary embodiment of a vision system.

Referring to FIG. 1, a vision system 1 may include a light emitting diode (LED) backlight 2 (i.e., lightbox panel), a robot 3, a bottle gripper tooling for the robot 4, a bottle 5, at least one camera 6, a flipper arm 7, a conveyer belt 8, and at least three photo-eyes for bottle position detection (not shown).

Bottles enter into the vision system 1 through the right side. The vision system 1 uses at least three photo-eyes (not shown) to detect the position of bottles in the vision system. For example, a first photo-eye may detect whether there is a bottle in the area that the robot arm will release the bottle. A second photo-eye may detect whether there is a bottle in an area right before the flipper arm 7. Lastly, a third photo-eye may detect whether there is a bottle at the entry of the vision system 1 (i.e., "third bottle in place"). For the vision system to be operational, the first photo-eye must detect that there is no bottle in the area that the robot arm will release the bottle. In other words, the first photo-eye must ensure that the path is clear for the robot arm to release the bottle. The second photo-eye must ensure that there is a bottle in the area right before the flipper arm 7. The second photo-eye must ensure that there is a bottle in the area right before the flipper arm 7 so that the robot 3 has a bottle to grab. Lastly, the third photo-eye must ensure that there is a third bottle in place so that it can be placed in position for the robot 3 when the bottle in the area right before the flipper arm gets grabbed by the robot 3. The vision system will only operate when the first photo-eye detects no bottles where the robot arm will drop a bottle, and the second photo-eye and the third photo-eye detects bottles at their respective positions before the flipper arm 7. The three photo-eyes may be discrete trigger signals, that do not travel over a network 15 (see FIG. 4).

However, embodiments are not limited to three photo-eyes. More or less photo-eyes may be used in order to ensure that a bottle is clear for the area where the robot 3 drops a bottle, and that bottles are in place at bottle queue positions (i.e., right before the flipper arm and at an area of the third bottle in place).

The LED backlight 2 of the vision system is used for defect detection. The LED backlight serves to silhouette any dark contamination on the surface of the bottle. Also, since light penetrates all sides of the bottle, the bottle appears to fluoresce. Therefore, as a result of the fluoresce, any gel (i.e., unmelted resin) or contaminate (i.e., carbon char, dust, etc.) within the wall of the bottle will appear darker due to the change in thickness. In other words, the change in thickness (i.e., density deviations) allows less light to escape when a bottle is subject to light from the LED backlight 2. The LED backlight 2 must be large enough to ensure that light penetrates all sides of the bottle. Therefore, the LED backlight 2 may be taller and wider than the bottle going through the vision system 1. However, embodiments of the LED backlight 2 are not limited to these features.

The robot 3 is a mechanical arm that is used with the bottle gripper tooling for the robot 4 to pick up the bottle from the top with four suction cups. After the robot 3 with the bottle gripper tooling for the robot 4 picks up the bottle, the bottle is rotated 360 degrees. Further, to increase efficiency of the vision system, the robot 3 may rotate the bottle at a speed of at least 120 rotations per minute (rpm). Rotating the bottle 360 degrees allows at least one camera 6 to take photos. In an exemplary embodiment, if the at least one camera 6 comprises multiple cameras positioned at different angles, each camera will be able to take pictures of the bottle at different sides and positions, during the bottle rotation. Each of the at least one camera 6 comprises an internal processor that is independently programmed. In addition, when the at least one camera 6 comprises multiple cameras, there is at least one camera for performing neck measurements. The at least one camera for performing neck measurements may measure the inner diameter, the outer diameter, and the threads of the bottle. The vision system will reject bad neck threads and bad sealing surfaces. As an example, if the bottle is rotated at 120 rpm, the process of picking up the bottle, rotating the bottle, and taking pictures by the at least one camera 6 will take approximately 1.7 seconds. However, embodiments are not limited. The robot 3 may be programmed to rotate at a faster or slow speed, and the at least one camera 6 may have different camera configurations. Further, the robot 3 may rotate the bottle at different rotation angles.

The bottle gripper tooling for the robot 4 is used to pick up the bottle from the top of the bottle with four suction cups fed from a single vacuum generator. The compressed air supply for the vacuum is fed through a rotary union 9. Further description of the bottle gripper tooling for the robot 4 will be described in FIG. 2. However, embodiments are not limited. The number of suction cups in the bottle gripper tooling of the robot 4 may be modified to enhance bottle pick up.

The flipper arm 7 is used to hold back the next bottle to be rotated by the robot 3. The flipper arm 7 is attached to a rotatory actuator 25 (see FIGS. 8 and 9). The rotary actuator 25 can turn both ways. The rotatory actuator 25 allows the flipper arm 7 to flip down (i.e., lie flat on the conveyer belt 8) when the robot 3 drops a bottle on the conveyer belt 8. The rotatory actuator allows the flipper arm to hold back (i.e., stop) the next bottle as soon as the bottle is picked up and moved by the robot 3. Further description of the flipper arm 7 will be described in FIGS. 3, 8-9.

The conveyer belt 8 allows for the bottles to move through the vision system. The conveyer belt 8 can be controlled manually or through automated processing. For example, the conveyer belt 8 may be stopped when the bottle is waiting to be picked up by the robot 3. After the robot 3 picks up a bottle, rotates it 360 degrees, and places the bottle down, the conveyer may be started again to move the next bottle up to be picked up by the robot. However, the conveyer belt 8 can be manually shut down by an operator. Further, the conveyer belt 8 may be automatically shut down when there is a large backup of bottles waiting to enter or exit the vision system. However, embodiments of the conveyer belt are not limited to these features.

The bottle 5 is an example of bottles used in the vision system. In an exemplary embodiment, the bottle 5 is not clear (i.e., not see through or transparent). Further, in the exemplary embodiment, the bottle 5 may have a non-uniform texture. The non-uniform texture may have ridges, bumps, or any other feature in which the surface is not smooth. However, embodiments are not limited to these features. The bottle 5 may be different sizes, have different textures, have different transparencies, and have different shapes.

Although FIG. 1 is a first exemplary embodiment of the vision system, a second exemplary embodiment of the vision system may be utilized. The second exemplary embodiment has a similar configuration to FIG. 1, with the exception that the second exemplary embodiment may also include a side conveyer 8' (illustrated in block diagram form). Thus, details of the features of the second exemplary embodiment that are the same as the features of the first exemplary embodiment in FIG. 1 will be omitted.

In the second exemplary embodiment, the side conveyer 8' may be provided at an entrance of the vision system. The side conveyer 8' may grasp the sides of the bottle 5 and suspend the bottle 5 in mid-air. The bottle 5 will be suspended in mid-air to prevent contamination from the conveyer belt 8 from being introduced on the bottom of the bottle 5. Thus, as the bottle enters the vision system, contamination that may occur on the conveyer belt 8 is prevented from being introduced in the bottle 5. The side conveyor 8' may grasp the sides of the bottle 5 with material that is more resistant to contamination than the conveyer belt 8. The length of the side conveyer 8' begins at the entrance of the vision system and ends right before the position where the bottle is waiting to be picked up by the robot 3. The side conveyer 8' may be operated by a variable frequency driver (VFD), so the user can start and stop bottles from being grabbed and held mid-air by the side conveyer. Starting and stopping the side conveyer 8' may prevent backups in the vision system. However, embodiments are not limited.

Although the second exemplary embodiment may have an entrance of the vision system at the right side of the vision system (see FIG. 1), embodiments are not limited. For example, the second exemplary embodiment may have the bottle 5 enter from the left side of the vision system. If the bottle 5 enters from the left side of the vision system, the length of the side conveyer 8' would begin at the left side of the vision system (i.e., entrance of the vision system) and end right before the position where the bottle is waiting to be picked up by the robot 3.

Figure 2:
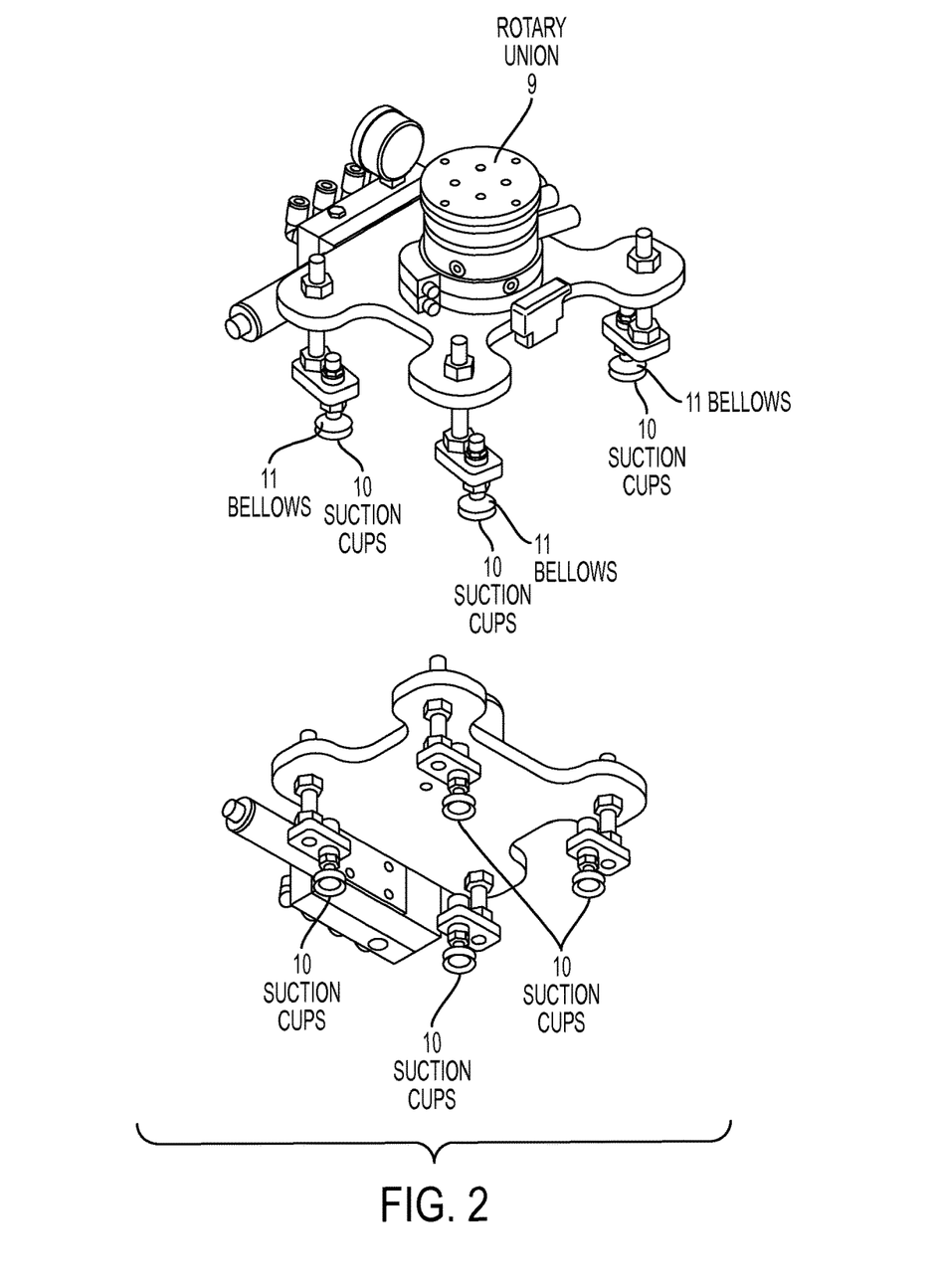
FIG. 2 is a diagram illustrating a bottle gripper tooling for a robot of the vision system in FIG. 1, according to the first exemplary embodiment.

FIG. 2 is a diagram illustrating the tooling for a robot of the vision system in FIG. 1, according to the first exemplary embodiment.

In FIG. 2, the bottle gripper tooling for the robot 4 may include the rotary union 9. The rotary union 9 allows for the bottle gripper tooling for the robot 4 to spin, while the rotary union 9 stays in place. The bottle gripper tooling for the robot also includes four suction cups 10. The four suction cups 10 are fed from a single vacuum generator (not shown). The compressed air is fed through the rotary union 9. Suction cups 10 allow for quick grasping of the bottle with a vacuum. Also, suction cups 10 allow for the bottle to be released quickly. Using suction cups allows for the bottle to be picked up and released faster than clamping. However, embodiments are not limited by the above features. The number of suction cups in the bottle gripper tooling for the robot 4 can be varied if a different bottle is used. Further, the bellows 11 above the suction cups work like an accordion to create a tight suction.

Figure 3:
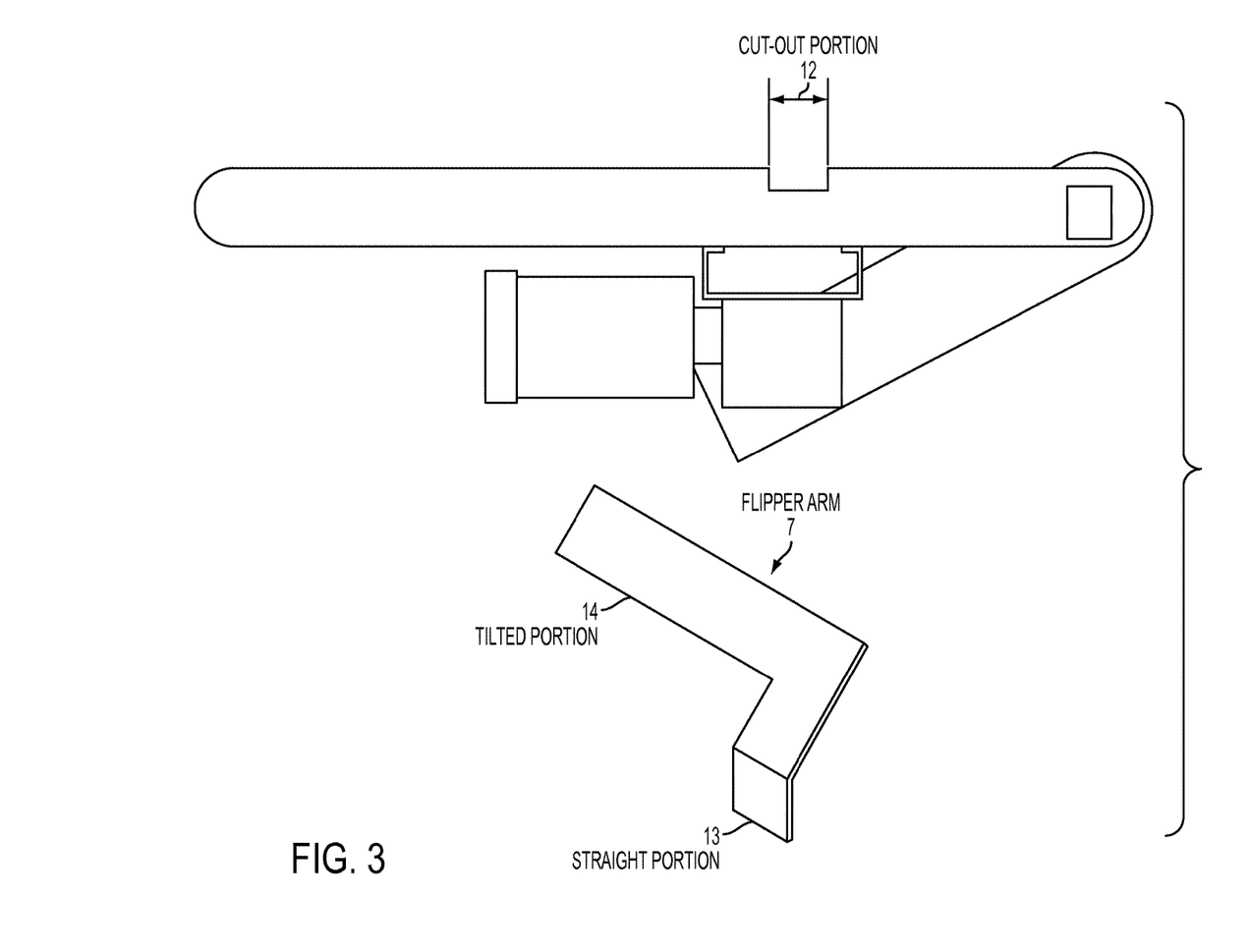
FIG. 3 is a diagram illustrating a flipper arm of the vision system in FIG. 1, and cut-out portion of a conveyer belt, according to the first exemplary embodiment.

FIG. 3 is a diagram illustrating a flipper arm of the vision system in FIG. 1, and a cut-out portion of the conveyer belt.

Figure 8:
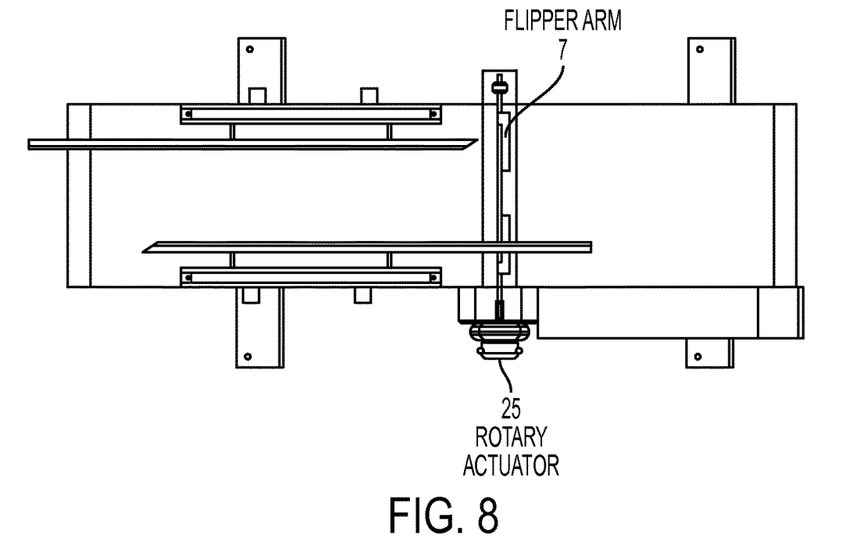
FIG. 8 is a diagram illustrating the flipper arm in FIG. 1, and rotary actuator.
Figure 9:
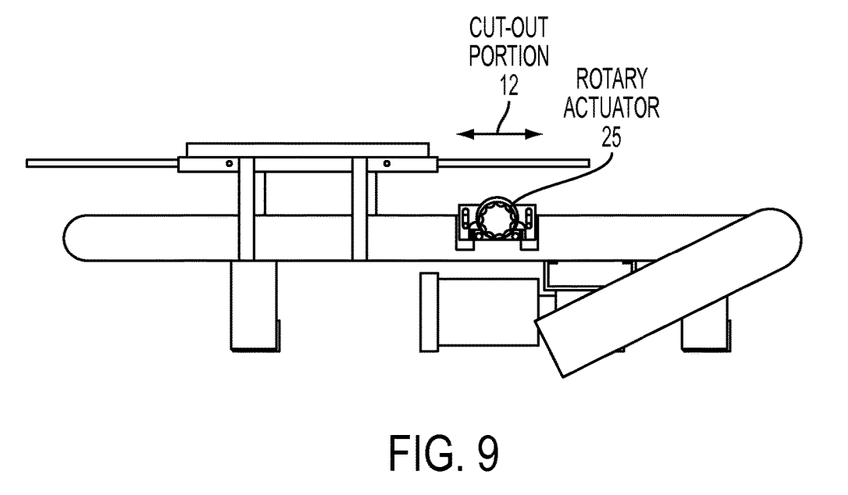
FIG. 9 is a diagram illustrating the cut-out portion of the conveyer belt, and rotary actuator.

In FIG. 3, the cut-out portion 12 of the conveyer belt 8 allows for the placement of the flipper arm 7 and the rotatory actuator 25 (see FIGS. 8-9). The rotatory actuator is placed in the cut-out portion 12, and attaches to the flipper arm 7. As shown in FIG. 3, the flipper arm 7 has a straight portion 13 and a tilted portion 14. The tilted portion 14 of the flipper arm 7 allows for the flipper arm 7 to hold back (i.e., stop) the next bottle or lay flat on the conveyer belt 8 to allow the bottle to pass through the conveyer belt. The flipper arm 7 is moved between holding back the next bottle and allowing the bottle to pass through rotation of the rotatory actuator 25 (see FIGS. 8-9). Rotating the rotatory actuator 25 moves the flipper arm 7 from the holding back position to the pass through position, and vice-versa. Therefore, the flipper arm 7 may hold back a bottle so that it is prevented from entering a position where the robot 3 releases the bottle.

The related art may include cylinder rods and popped up pins for stopping bottles. However, the related art (i.e., cylinder rods and pins) are not fast enough to hold back bottles in the vision system. Therefore, the configuration of the flipper arm 7 and the rotatory actuator 25 overcomes the disadvantages of the related art.

Figure 4:
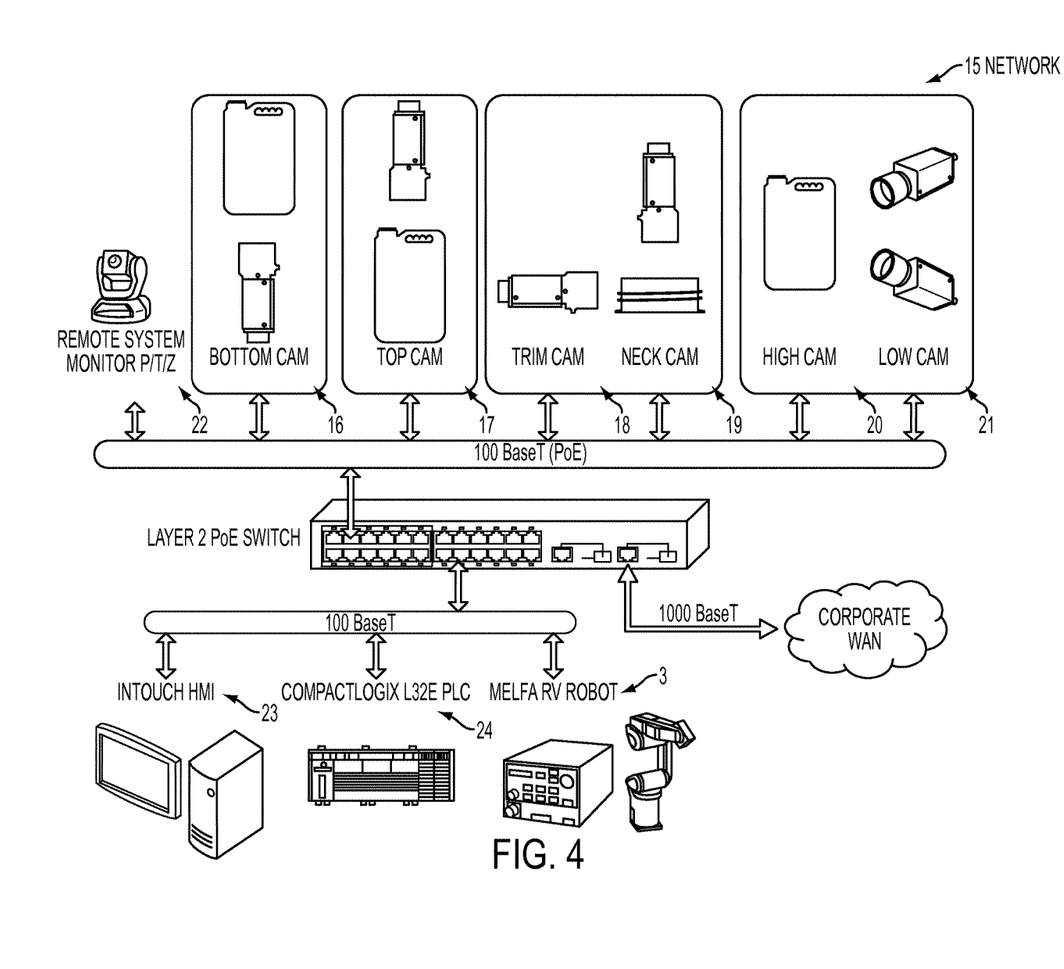
FIG. 4 is an overall network configuration of the vision system of the exemplary embodiments.

FIG. 4 is an overall network configuration of the vision system of the exemplary embodiments.

In FIG. 4, components of the network 15 of the vision system may communicate with each other over the Ethernet. As shown in FIG. 4, the network 15 is a Power-Over-Ethernet (POE) 100 BaseT network. However, the network 15 is not limited. The components of the vision system may communicate over any wired or wireless network system. One example of a wireless network system is Wi-Fi. Further, the network 15 can be modified by one of ordinary skill in the art, in order to reduce communication times, reduce costs, or improve signal quality. Thus, the configuration of the network 15 is shown as a non-limiting example of the network 15 of the vision system.

In FIG. 4, the network 15 of the vision system may comprise a bottom camera 16 for inspecting the bottom of the bottle, a top camera 17 for inspecting the top of the bottle, a trim camera 18 for inspecting the trim of the bottle, a neck camera 19 for inspecting the neck of the bottle, a high camera 20 for inspecting the top half of the bottle, and a low camera 21 for inspecting the bottom half of the bottle. The cameras shown in FIG. 4 may be part of the at least one camera 6. Further, the network 15 of the vision system 15 may include a remote system monitor 22. The remote system monitor 22 may allow a user to observe the vision system from remote locations. The network 15 may also include an InTouch Human Machine Interface (HMI) 23. As shown in FIG. 4, the HMI 23 may include a touch screen interface for controlling the vision system. The HMI 23 may perform camera initialization, record reject locations, and count statistical data. Further, a programmable logic controller 24 of the network 15 may manage bottling handling and/or rejecting, and interfacing with the robot 3. Further, the network 15 may include a corporate wide area network (WAN), for interfacing with the corporate network. However, the network 15 of the vision system may be modified. As an example, the network 15 may have less or more cameras than are shown in FIG. 4. Further, the robot 3, the PLC 24, and the InTouch HMI may be substituted with components that perform the same or similar functions, and such substitutions would be within the knowledge of one of ordinary skill in the art.

Figure 5:
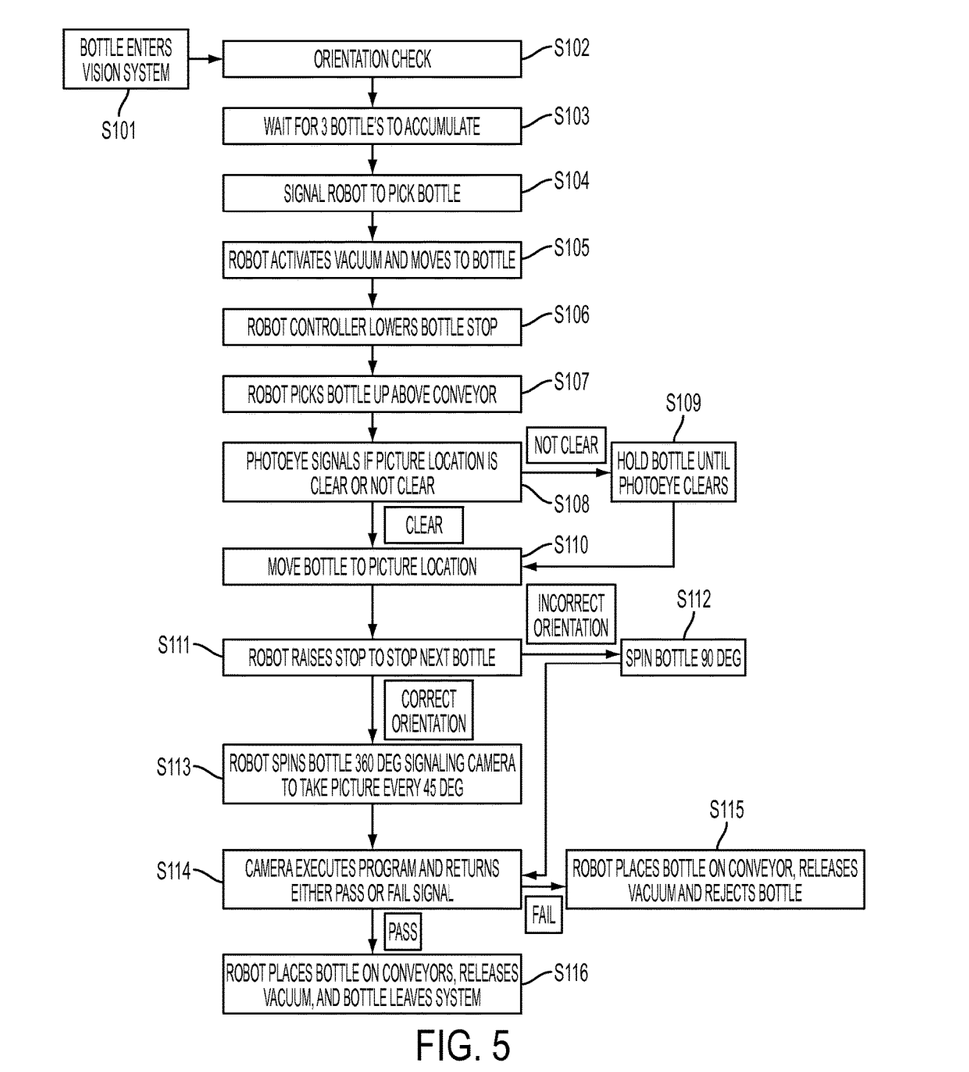
FIG. 5 is a flowchart illustrating a process of detecting defects in the vision system according to the exemplary embodiments.

FIG. 5 is a flowchart illustrating the process of detecting defects in the vision system according to the exemplary embodiments.

In Step S101, a bottle enters the vision system. In Step S102, an orientation check is performed to ensure that all cameras and photo-eyes are in position and functioning properly. In Step S103, the vision system waits for three bottles to accumulate (i.e., the first photo-eye ensures that no bottles are in a position where the robot 3 releases the bottle, the second photo-eye ensures that there is a bottle in an area right before the flipper arm 7, and a third photo-eye ensures that there is a bottle at the entry of the vision system 1). If the vision system receives the correct signals from all three photo-eyes (Step S104), the robot 3 actives the vacuum and moves toward the bottle (Step S105). In Step S106, the robot 3 lowers toward the bottle and places its four suction cups on the bottle. In Step 107, the robot 3 picks the bottle up above the conveyer belt 8.

Then, the robot 3 checks the first photo-eye to ensure that there is no bottle at the release position (Step S108). If there is a bottle at the bottle release position, the bottle is held by the robot 3 until the bottle release position is cleared (Step S109), and then the bottle is moved to the bottle release position (Step S110). If there is no bottle at the bottle release position, the bottle is moved to the bottle release position (Step S110).

Then, the flipper arm 7 stops the next bottle (Step S111) when the bottle is moved to the bottle release position. If the bottle is at an incorrect orientation, the bottle is spun 90 degrees (Step S112), and the camera executes the program to return either a pass or a fail signal for the bottle (Step S114). If the bottle is at a correct orientation, the robot spins the bottle at 360 degrees, and signals the at least one camera 6 to take pictures at every 45 degrees of the 360 degree bottle rotation (Step S113). Then, the at least one camera 6 executes the program to return either a pass or a fail signal for the bottle (Step S114). If the fail signal is returned, the robot 3 places the bottle on the belt conveyer 8, releases the vacuum, and rejects the bottle by a blow off cylinder (Step S115). If the pass signal is returned, the robot 3 places the bottle on the belt conveyer 8, releases the vacuum, and the bottle leaves the vision system 1 (Step S116). After Step S116, the flowchart is repeated for the next bottles.

Figure 6:
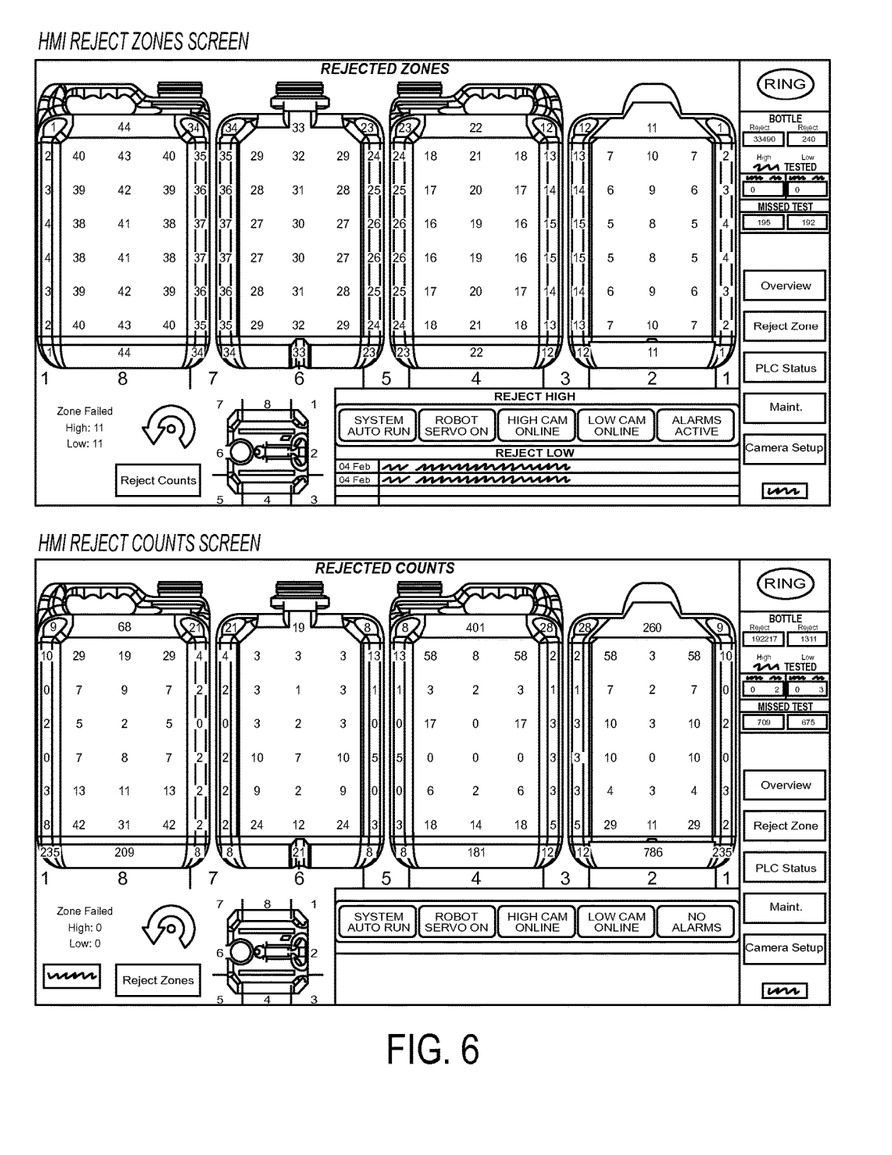
FIG. 6 is a diagram illustrating defect region detection of the exemplary embodiments.

FIG. 6 is a diagram illustrating defect region detection of the exemplary embodiments.

FIG. 6 shows an example of the pictures taken by the at least one camera 6. As shown in FIG. 6, the reject zones are displayed on a display unit. FIG. 6 shows the bottle at different angles taken by the at least one camera 6. For example, a picture can be taken at on the right side, left side, front, and back side of the bottle. As shown in FIG. 6, each of the pictures taken can be divided into "rejected zones". Then, each of the rejected zones is analyzed to determine whether a defect has occurred in the rejected zone. As shown in FIG. 6, one defect occurred at rejected zone 11. More detail of the method of detecting defects using the defect region detection will be described in FIG. 7.

Figure 7:
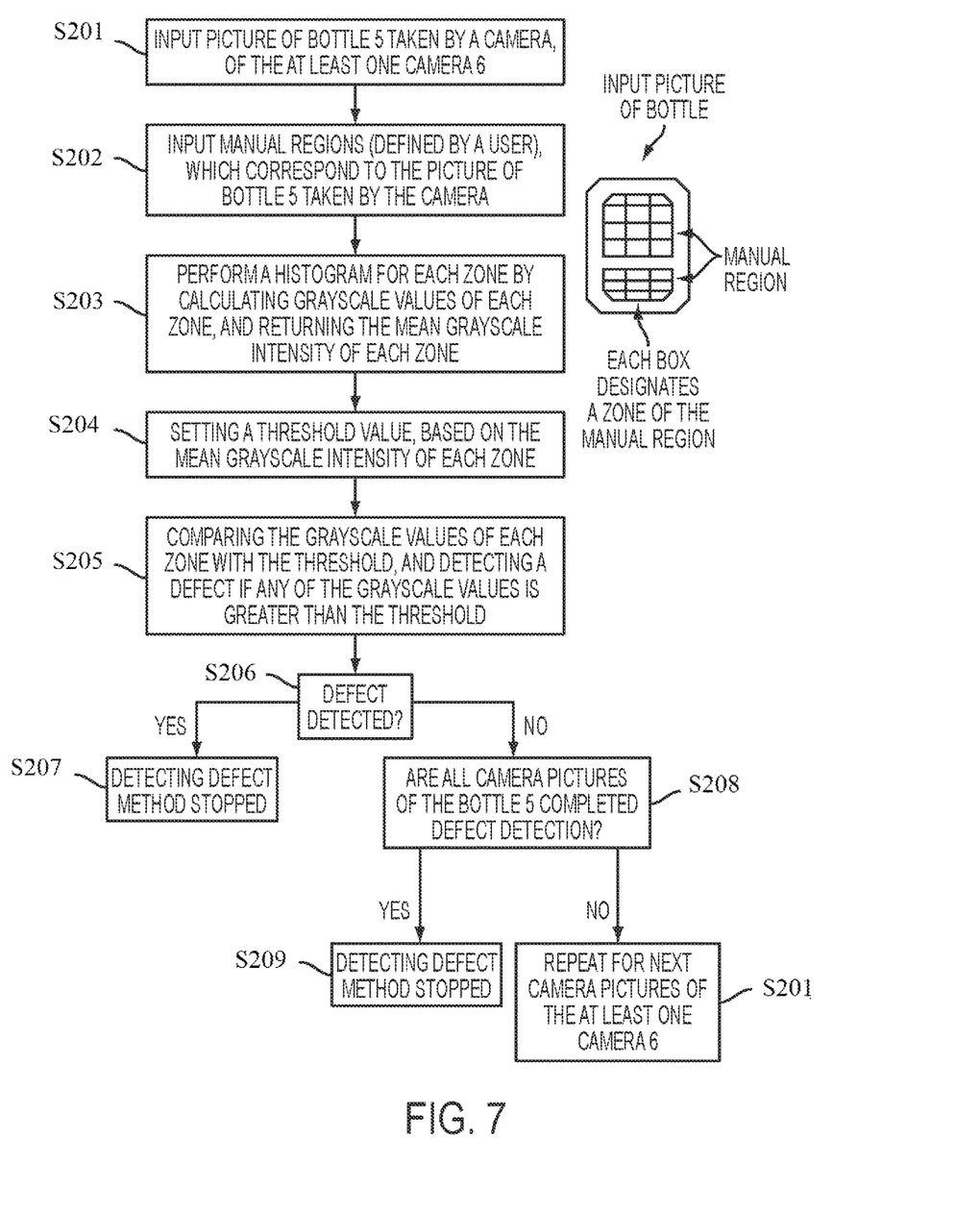
FIG. 7 is a flowchart illustrating a method of detecting defects using the defect region detection.

FIG. 7 is a flowchart illustrating a method of detecting defects using the defect region detection.

In Step S201, a camera picture of the bottle 5 is input. The camera picture is from the at least one camera 6. In Step S202, manual regions are input, which correspond to the inputted camera picture of the bottle 5. As shown to the right of Step S202, manual regions may correspond to the shape of the inputted camera picture. Manual regions are defined by a user of the defection detection system. The user defines manual regions in order to exclude regions of the bottle 5 which always have a higher grayscale value (i.e., darker region) than the remaining portions of the bottle 5. If manual regions are not defined in the embodiments, false positives (i.e., incorrect defects detected) of the vision system may occur.

One of ordinary skill in the art would understand that manual regions may be modified by the user in order to enhance precision. As a first example, the manual regions may be defined as a plurality of zones. In the first example, the plurality of zones is predefined by the user. As a second example, there could be a large manual region and a small manual region. In the second example, the small manual region may correspond to the shape of the large manual region. Therefore, the small manual region may move through the large region in a sweeping or looping fashion, until all of the grayscale values are calculated for every part of the large region. However, embodiments are not limited.

In Step S203, a histogram is performed for each zone by calculating grayscale values in each zone (i.e., light intensity variations). In particular, grayscale values are calculated for each zone by "sweeping through" (i.e., moving from left to right and line by line) each zone and calculating grayscale values at predetermined interval points of each zone. One of ordinary skill in the art would understand that the interval points can be modified to return a large or a small number of calculated grayscale values. Further, in Step S203, the mean grayscale intensity of the entire zone is returned. In Step S203, a histogram graph may be displayed to the user of the defect detection system. Further, the histogram graph may be displayed to the user at any point when the grayscale values have been calculated for each zone. Grayscale values may include contrast, dark count, bright count, and other measures for light intensity. However, embodiments are not limited.

In Step S204, a threshold value is determined based on the mean grayscale intensity of the entire zone. In Step S205, the grayscale values in each zone are compared with the threshold value. Further, in Step S205, a detect will be detected if any of the grayscale value in each zone are greater than the threshold value.

In Step S206, it is determined whether a defect is detected. If a defect is detected, the detecting defect method is stopped (Step S207). Therefore, the bottle is rejected. One of ordinary skill in the art would understand that if the detecting defect method is stopped after only one defect is detected, processing resources are minimized. Further, in a majority of applications of the vision system, the vision system only needs to determine whether the bottle 5 has a defect or not. Therefore, the vision system does not need to detect multiple defects in the bottle 5. However, embodiments are not limited. The vision system may be modified by the user to detect multiple defects in the bottle 5.

However, if defects are not detected, it is determined whether all camera pictures of the at least one camera 6 have completed defect detection (Step S208). If all camera pictures have completed defect detection, the detecting defect method is stopped for the bottle 5 (Step S209). If not all camera pictures of the at least one camera 6 have completed defect detection, then the method is returned to Step S201 for the next camera picture. Further, when all camera pictures have completed defect detection, the process is then repeated for the next bottle.

FIG. 7 is a flowchart illustrating a method of detecting defects using the defect region detection method. Although FIG. 7 shows defecting defects for one bottle 5, one of ordinary skill in the art would readily understand that the process is repeated for all of the bottles that enter the vision system.

FIG. 8 is a diagram illustrating the flipper arm in FIG. 1, and rotary actuator.

In FIG. 8, the rotary actuator 25 rotates to move the flipper arm 7 between holding back the next bottle or allowing the bottle to pass, through rotation of the rotary actuator 25. Rotating the rotary actuator 25 moves the flipper arm 7 from the holding back position to the pass through position, and vice-versa. Therefore, the flipper arm 7 may hold back a bottle so that it is prevented from entering a position where the robot 3 releases the bottle. The flipper arm 7 is moved between holding back the next bottle or allowing the bottle to pass through rotation of the rotary actuator 25.

FIG. 9 is a diagram illustrating the cut-out portion of the conveyer belt, and rotary actuator.

In FIG. 9, the rotary actuator 25 may be placed in the cut-out portion of the conveyer belt (see FIG. 3). Therefore, the rotary actuator 25 is integrated with the conveyer belt 8, and allows the flipper arm to move back and forth between holding back the bottle and allowing the bottle to pass through the flipper arm 7.

Although not shown in the drawings, the vision system may also include a vacuum brake. The vacuum brake can slow down the bottles as they enter the conveyer belt 8. This ensures that the vision system does not get jammed with bottles at the entrance of the vision system. In comparison to related art braking systems, which may dent the bottles, the vacuum brake applies suction for slowing down the bottles. The vacuum brake may also ensure that only three bottles are in the vision system at one time. However, embodiments are not limited.

Although not shown in the drawings, the vision system may also include a blow off cylinder at the exit of the vision system. The blow off cylinder may push rejected bottles (i.e., bottles with detected defects) off the conveyer belt, and into a "rejected bottle container".

Although embodiments of the vision system are primarily used for detecting defects on the surface and inside the bottles, the vision system may be also used to reject neck threads and bad neck sealing surface with the at least one camera 6.

As compared to the related art, the embodiments are faster, use less floor space, can detect defects in the bottles with a higher precision, can detect more defects in the bottles, and can aid in identifying sources of bottle contamination.

The foregoing is illustrative of example embodiments and is not to be construed as limiting thereof. Although a few example embodiments have been described, those skilled in the art will readily appreciate that many modifications are possible in the exemplary embodiments without materially departing from the novel teachings and advantages of the embodiments. Accordingly, all such modifications are intended to be included within the scope of the embodiments as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of detecting defects in a vision system, comprising:
    obtaining at least one bottle of a material comprising glass, transparent plastic, or non-transparent plastic for determining a defect, wherein determining the defect of the at least one bottle is operational on glass bottles, transparent bottles and non-transparent bottles;
    taking a picture of the at least one bottle using at least one camera as the at least one bottle rotates 360 degrees relative to the at least one camera;
    inputting the picture;
    inputting manual regions that correspond to the imputed picture and excluding regions of the at least one bottle having a grayscale value higher than a predetermined value, each manual region being defined by a plurality of zones, which correspond to the picture taken by the at least one camera;
    performing a histogram by calculating grayscale values of each zone;
    setting a threshold value of each zone based on the histogram for determining the defect;
    comparing the threshold value of each zone with the calculated grayscale values; and
    rejecting the at least one bottle if any of the calculated grayscale values is greater than the threshold value of each zone,
    wherein the setting threshold value based on each zone based on the histogram further comprises:
        calculating a mean grayscale value of each zone based on the grayscale values calculated for the histogram; and
        setting the threshold value based on the mean grayscale value of each zone, and
    wherein the performing the histogram by calculating grayscale values of each zone further comprises sweeping through each zone and calculating grayscale values at predetermined, non-adjacent interval points of each zone.

2. The method of detecting defects as claimed in claim 1, wherein the manual regions are defined by a user.

3. The method of detecting defects as claimed in claim 1, wherein regions having a grayscale value that is less than the predetermined value are included in the manual regions.

4. The method of detecting defects as claimed in claim 1, wherein the manual regions correspond to the picture by having a same shape as the picture taken by the at least one camera.

5. The method of detecting defects as claimed in claim 1, further comprising:
    stopping the defect detection when the at least one bottle is rejected.

6. The method of detecting defects as claimed in claim 1, further comprising:
    repeating the defect detection for another picture taken by at least one camera when the at least one bottle is not rejected.

7. A method of detecting defects in a vision system, comprising:
    obtaining at least one bottle of a material comprising glass, transparent plastic, or non-transparent plastic for determining a defect, wherein determining the defect of the at least one bottle is operational on glass, transparent bottles and non-transparent bottles;
    measuring an inner diameter, an outer diameter and threads of the at least one bottle using a neck camera;
    rejecting the at least one bottle if the threads or sealing surfaces of the at least one bottle are insufficient based on the measurements of the inner diameter, the outer diameter and the threads;
    activating a vacuum of a robot moving the robot toward the at least one bottle to place suction cups on the at least one bottle to lift the at least one bottle of a surface;
    taking a picture of the at least one bottle using at least one camera while the robot rotates the at least one bottle 360 degrees relative to the at least one camera with the at least one bottle in an upright position;
    inputting the picture;
    inputting manual regions that correspond to the inputted picture and excluding regions of the at least one bottle having grayscale value higher than a predetermined value, the manual region comprising a large manual region and a small manual region for sequentially sweeping through the large manual region, the small region corresponding to the large manual region;
    performing histogram by calculating grayscale values of each small region;
    setting a threshold value of each small region based on the histogram for determining the defect;
    comparing the threshold value of each small region with the calculated grayscale values; and
    rejecting the at least one bottle if any of the calculated grayscale values is greater than the threshold value of each small region,
    wherein the setting the threshold value based on each small manual region based on the histogram further comprises:
        calculating a mean grayscale value of each small manual region based on the grayscale values calculated for the histogram; and
        setting the threshold value based on the mean grayscale value of each small manual region, and wherein the performing the histogram by calculating grayscale values of each small region further comprises sweeping each small manual region through the large manual region and calculating grayscale values at pre-determined, non-adjacent interval points of each small manual region.

8. The method of detecting defects as claimed in claim 7, wherein the small manual region corresponds to the large manual region by having a same shape.

9. The method of detecting defects as claimed in claim 7, wherein the large manual region corresponds to the picture by having a same shape as the picture taken by the at least one camera.

* * * * *